(12) United States Patent
Borm et al.

(10) Patent No.: US 10,556,075 B2
(45) Date of Patent: Feb. 11, 2020

(54) METHOD AND APPARATUS FOR THE REMOVAL OF ANAESTHETIC AGENTS FROM BREATHING GAS

(75) Inventors: Pieter Borm, Eindhoven (NL); Bart Westerkamp, Alkmaar (NL)

(73) Assignee: LÖWENSTEIN MEDICAL TECHNOLOGY S.A, Luxembourg (LU)

( * ) Notice: Subject to any disclaimer, the term of this patent is extended or adjusted under 35 U.S.C. 154(b) by 0 days.

(21) Appl. No.: 13/500,214

(22) PCT Filed: Oct. 6, 2010

(86) PCT No.: PCT/NL2010/000141
§ 371 (c)(1),
(2), (4) Date: Jun. 21, 2012

(87) PCT Pub. No.: WO2011/043649
PCT Pub. Date: Apr. 14, 2011

(65) Prior Publication Data
US 2012/0266881 A1      Oct. 25, 2012

(30) Foreign Application Priority Data

Oct. 7, 2009 (NL) ...................................... 1037371

(51) Int. Cl.
*A61M 16/01* (2006.01)
*A61M 16/22* (2006.01)
(Continued)

(52) U.S. Cl.
CPC ...... *A61M 16/009* (2013.01); *A61M 16/0045* (2013.01); *A61M 16/0057* (2013.01);
(Continued)

(58) Field of Classification Search
CPC .. A61M 16/01; A61M 16/22; A61M 16/0883; A61M 16/0891; A61M 16/0057;
(Continued)

(56) References Cited

U.S. PATENT DOCUMENTS 5,398,675 A * 3/1995 Henkin ................. A61M 16/01
128/203.12
5,520,169 A * 5/1996 Georgieff et al. ....... 128/204.16
(Continued)

FOREIGN PATENT DOCUMENTS

DE       102004033588 A1    2/2006
EP             1356840 A1   10/2003
(Continued)

OTHER PUBLICATIONS

International Search Report for corresponding International Application No. PCT/NL2010/000141.

*Primary Examiner* — Tu A Vo
(74) *Attorney, Agent, or Firm* — Egbert, McDaniel & Swartz, PLLC

(57) ABSTRACT

A method for al of a volatile anesthetic agent from a breathing gas in a respirating apparatus includes the steps of leading at least a portion of the breathing gas through a portion of a line system in which the portion of the line system has a filter therein, cooling the breathing gas to a temperature below a temperature of the boiling point of the anesthetic agent when the breathing gas passes through the filter so as to condense the anesthetic agent out of the breathing gas, warming the breathing gas after the anesthetic agent is condensed, and leading the warmed breathing gas out of the portion of the line system back into the line system. The filter has activated carbon therein.

11 Claims, 1 Drawing Sheet

(51) Int. Cl.
*A61M 16/00* (2006.01)
*A61M 16/08* (2006.01)
*A61M 16/10* (2006.01)

(52) U.S. Cl.
CPC .... *A61M 16/0066* (2013.01); *A61M 16/0093* (2014.02); *A61M 16/01* (2013.01); *A61M 16/0891* (2014.02); *A61M 16/104* (2013.01); *A61M 16/22* (2013.01); *A61M 2202/0021* (2013.01); *A61M 2202/0241* (2013.01); *A61M 2205/36* (2013.01); *A61M 2205/3606* (2013.01); *A61M 2205/3673* (2013.01)

(58) Field of Classification Search
CPC .............. A61M 16/0066; A61M 16/00; A61M 16/0063; A61M 16/0087; A61M 16/009; A61M 16/0093; A61M 16/10; A61M 16/104; A61M 16/18; A61M 16/20; A61M 16/201; A61M 16/202; A61M 16/205; A61M 16/204
USPC ............ 128/200.11, 200.24, 201.13, 201.25, 128/201.28, 203.12, 203.13, 203.15, 128/203.16, 203.18, 203.25, 203.26, 128/203.27, 203.29, 204.15, 204.16, 128/204.17, 204.18, 205.12, 205.19, 128/205.24, 205.27, 205.28, 205.29, 128/207.14
See application file for complete search history.

(56) References Cited

U.S. PATENT DOCUMENTS

| | | | | |
|---|---|---|---|---|
| 6,131,571 | A * | 10/2000 | Lampotang et al. | 128/204.21 |
| 6,523,538 | B1 * | 2/2003 | Wikefeldt | 128/204.18 |
| 6,745,771 | B2 * | 6/2004 | Castor et al. | 128/205.27 |
| 7,814,908 | B2 * | 10/2010 | Psaros | 128/205.28 |
| 2004/0216743 | A1 * | 11/2004 | Orr | A61M 16/0045 128/205.12 |
| 2006/0196505 | A1 * | 9/2006 | Izuchukwu | A61M 16/0051 128/203.15 |
| 2006/0254586 | A1 * | 11/2006 | Berry | A61M 16/009 128/204.16 |
| 2006/0254587 | A1 * | 11/2006 | Berry | A61M 16/009 128/204.16 |
| 2006/0254590 | A1 * | 11/2006 | Berry | A61M 16/009 128/205.12 |
| 2007/0157929 | A1 * | 7/2007 | Radomski et al. | 128/204.18 |
| 2008/0283059 | A1 * | 11/2008 | Siegel et al. | 128/203.25 |
| 2010/0212668 | A1 * | 8/2010 | Flanagan | A61M 16/104 128/203.16 |

FOREIGN PATENT DOCUMENTS

| | | |
|---|---|---|
| WO | 0107108 A1 | 2/2001 |
| WO | 2004060459 A1 | 7/2004 |

* cited by examiner

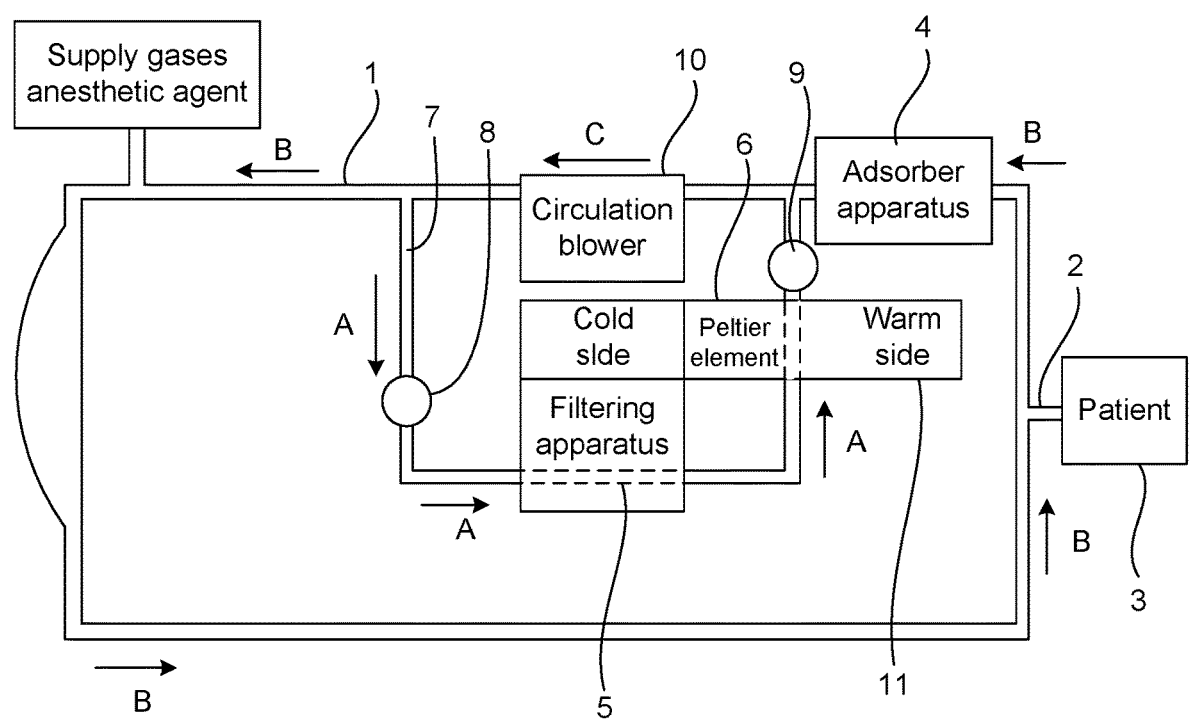

METHOD AND APPARATUS FOR THE REMOVAL OF ANAESTHETIC AGENTS FROM BREATHING GAS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to a method for the removal of volatile anesthetic agents from breathing gas in an apparatus for respirating of patients provided with a line or conduit system in which breathing gas can be circulated, comprising leading the breathing gas or a part thereof through a filtering apparatus with activated carbon, whereby the breathing gas is cooled when passing through the filtering apparatus.

2. Description of Related Art Including Information Disclosed Under 37 CFR 1.97 and 37 CFR 1.98.

Such a method is known.

By cooling the breathing gas, for instance to a temperature below 21° C., an anesthetic agent having a boiling point below 21° C. will condense, and the activated carbon can adsorb much more than in gaseous condition.

From the European patent application EP 1 356 840 A is known a filtering apparatus with a filter element with means for adjusting the temperature of the element, for instance for the cooling of the ingoing gas or the element itself, whereby the aim is to improve the absorption by the filter of anesthetic agent. With this apparatus further means are provided to warm the gas again, whereby the warmed gas is led again through the filter and again absorbs anesthetic agent that is supplied to the patient. In this manner re-use of the anesthetic agent is possible.

This application further describes that gas intended for inhalation by a patient who is to be waken up, and which gas for this reason must not contain anesthetic agent, is led through the filter cooled, to avoid the gas absorbing anesthetic agent from the filter.

This apparatus has the drawback, that the patient is supplied with breathing gas that is cooled and that is not humid enough.

The invention aims to obviate this drawback.

BRIEF SUMMARY OF THE INVENTION

The method according to the invention to that end is characterized, in that the breathing gas, after this has been led through the filtering apparatus with activated carbon, is warmed.

With the invention it is attained that the temperature of the breathing gas coming out of the filter gets to be approximately the same as the temperature of the breathing gas in the system of the respirating apparatus.

According to a further characteristic of the method according to the invention the breathing gas, after anesthetic agent has been condensed out of it, is warmed immediately after the passing through the filtering apparatus.

Hereby the breathing gas is cooled in the apparatus and at the same time warmed at another location, as a result of which no total cooling off or substantial warm up takes place. Suitable for application with this method is any device by means of which a cooling can take place and more or less at the same time at another location a warming can take place, such as the application of heat pump, a heat pipe, a thermopile, a Peltier element, and such like.

According to a further characteristic of the method according to the invention breathing gas is circulated in the line system by means of a circulation blower.

According to a further characteristic of the method according to the invention breathing gas is lead into a line system part, which line system part is provided with the filtering apparatus, and which part is connected to the line system, while the breathing gas in the line system is circulated in such a way, that the duration of one circulation of the breathing gas in the line system is substantially shorter than the duration of one circulation of the breathing gas in the line system part that is provided with the filtering apparatus.

According to a further characteristic of the method according to the invention the breathing gas is circulated in the line system at such a speed, that the duration of one circulation of the gas is 10 seconds at the most, more in particular is 5 seconds at the most, more in particular is 3 seconds at the most, and still more in particular is 2.5 seconds at the most.

With this it is attained that with the giving off of moisture by the $CO_2$ absorber provided in the line system the breathing gas within a short time again is completely saturated with water vapour, so that the patient breathes in breathing gas that is more or less at bodily temperature and that is sufficiently humid.

The invention further relates to an apparatus for the application of the method according to the invention, which apparatus is provided with means by which a breathing gas can be circulated in a line or conduit system and the pressure in the line system can be varied in accordance with a certain respirating pattern, with a connecting means for the patient and with connections for the supply of the various components of the breathing gas, whereby the apparatus further is provided with a filtering apparatus with activated carbon for the removing of volatile anesthetic agents that are present in the line system, whereby the filtering apparatus is provided with means by which the breathing gas, when it passes through the filtering apparatus, can be cooled, in such a way, that anesthetic agent condenses onto the activated carbon, characterized in that the apparatus is provided with means by which breathing gas, after this has been lead through the filtering apparatus with activated carbon, is warmed.

According to a further characteristic of the apparatus according to the invention the apparatus is provided with means by which the breathing gas, immediately after the cooling thereof, can be warmed.

According to yet another characteristic of the apparatus according to the invention the means by which the breathing gas can be cooled as it passes through the filtering apparatus are formed by a heat pump.

According to a further characteristic of the apparatus according to the invention the means are formed by a Peltier element.

According to another characteristic of the apparatus according to the invention the means are formed by a heat pipe.

According to another characteristic of the apparatus according to the invention the means are formed by a thermopile.

With the method and apparatus according to the invention the breathing gas is cooled and led through the filtering apparatus whereby the anesthetic agent is absorbed by the filter.

Thereafter the gas is warmed but not led through the filter one more time and therefore not provided again with anesthetic agent. The patient is supplied with warmed breathing gas.

According to a further characteristic of the apparatus according to the invention in the line system an absorber apparatus is provided for withdrawing from the breathing gas of carbon dioxide exhaled by the patient.

According to a further characteristic of the apparatus according to the invention the line system is provided with a circulation blower.

According to a further characteristic of the apparatus according to the invention a line system part, with in it the filtering apparatus, is connected to the line system, with a closing means for opening and closing the access for breathing gas out of the line system into the line system part, while the line system is provided with a circulation blower having a capacity that is adapted to the volume of the line system in such a way, that the duration of one circulation of the gas is 10 seconds at the most, more in particular 5 seconds at the most, more in particular 3 seconds at the most, and more in particular is 2.5 seconds at the most.

The invention will now be described further with reference to the drawing of an example of an embodiment.

BRIEF DESCRIPTION OF THE SEVERAL VIEWS OF THE DRAWINGS

FIG. 1 is a schematic view of an embodiment of the present invention.

DETAILED DESCRIPTION OF THE INVENTION

As is shown in the drawing the apparatus for the respirating of patients, more in particular for anesthesia, comprises a line system 1 for the breathing gas with a connecting means 2 for the patient 3 and with connecting means (not shown) for the supply of the various components of the breathing gas, such as oxygen and an anesthetic agent, with an absorber apparatus 4 for the withdrawing from the breathing gas of the carbon dioxide exhaled by the patient. The apparatus further is provided with a filtering apparatus 5 with activated carbon for the removing of volatile anesthetic agents that are present in the line system 1, whereby the filtering apparatus 5 is provided, in this embodiment, with a Peltier element 6 by means of which the breathing gas as it passes through the filtering apparatus 5 can be cooled. In the drawing is shown a closed system, by means of which the patient is respirated or breathed upon.

A line system part 7, that is provided with the filtering apparatus 5, is connected to the line system 1, whilst the closing means 8 and 9 are provided for the opening and closing and allowing of access of breathing gas according to the arrow A out of the line system 1 to and through the line system part 7. The line system 1 is provided with a circulation blower 10.

In the system shown the breathing gas circulates from the patient 3 in the line system 1 in one direction according to the arrow B. The gas hereby passes the circulation blower 10. Thereafter the gas flow is divided into a part according to the arrow B through the whole of the line system 1 and a part according to the arrow A through the line system part 7 in which the filtering apparatus 5 is provided. The incoming gas and the activated carbon in the filtering apparatus are cooled by the Peltier element 6. This pumps the heat from the cold side 5 to the warm side 11, where the gas that is lead back takes on again the temperature of the gas circulating in the part 1 of the system as a result of the heat transfer from the warm side of the Peltier element. The Peltier element 6 extracts warmth from the incoming gas via the activated carbon. It is intended that the volatile anesthetic agent condenses upon the activated carbon and not at another location. To the outgoing gas the extracted warmth is fed back again so that the temperature of the breathing gas is approximately that of the respiratory system.

The capacity of the circulation blower 10 is adapted to the volume of the line system 1 in such a way, that the duration of one circulation of the gas in the line system 1 is 10 seconds at the most, more in particular 5 seconds at the most, more in particular 3 seconds at the most, and yet more in particular 2.5 seconds.

Taking 2.5 seconds as a guiding principle, in the case of for instance a volume of the line system 1 of 2.5 litre a circulation blower 10 having a capacity of 60 litre per minute has to be applied. This leads to a duration of a circulation of: 2.5 liter/60 liter/min=0.042 minutes=2.5 seconds.

Again taking 2.5 seconds as a guiding principle, in the case of for instance a volume of the line system 1 of 1.25 litre a circulation blower having a capacity of 30 litre per minute has to be applied, in the case of a volume of the line system of 5 litre a circulation blower having a capacity of 120 litre per minute has to be applied, and in the case of a volume of the line system of 0.625 litre a circulation blower having a capacity of 15 litre per minute has to be applied.

In the example of the embodiment shown the capacity of the circulation blower 10 is 60 litre per minute. The circulation blower 10 brings about a flow in the line system 1 in the part indicated by the arrow C of approximately 60 litre per minute. In the other part of the line system 1 indicated with the arrows B the flow is about 50 litre per minute.

The pneumatic resistance of the line system part 7 with in it the filtering apparatus 5 is, in the example of the embodiment shown, about five times greater than the pneumatic resistance of the line system 1 or rather the main line or conduit 1.

In the line system part 7 indicated with the arrow A the flow is much lower and can vary between 8 litre per minute and 12 litre per minute. Depending on the volume of the line system part 7 the duration of one circulation of the gas in the line system part 7 can take 25 seconds.

With the application of a circulation blower 10 having a capacity that is adapted to the volume of the circuit it is attained that with the giving off of moisture by the $CO_2$ absorber 4 provided in the line system 1 the breathing gas coming out of the line system part 7 during the circulation and mixing in the line system 1 within a short time again is completely saturated with water vapour, so that the patient breathes in breathing gas that is more or less at bodily temperature and that is sufficiently humid.

With the apparatus according to the invention in an effective manner volatile anesthetic agents having a low boiling point can be eliminated.

The gas coming into the filtering apparatus has a relatively high humidity level, so that, when it is cooled in the filtering apparatus, water will condense in the activated carbon.

The invention provides for it that the exit for the breathing gas is disposed at a lower level than the entry, so that this water can be discharged from the filtering apparatus.

We claim:

1. A method for removal of a volatile anesthetic agent from breathing gas in an apparatus for respirating patients, the apparatus having a line system for circulating the breathing gas in which the line system has a blower therein, the line system having a main portion, a first portion communicating with the main portion and a second portion communicating with the main portion, the first portion positioned parallel to the second portion, the method comprising:

leading all of the breathing gas through the main portion of the line system in which the main portion of the line system has an absorber therein for withdrawing carbon dioxide so as to remove the carbon dioxide from the breathing gas;

leading at least a portion of the breathing gas through the second portion of the apparatus, in which the second portion has a filter therein, the filter having activated carbon therein, the absorber and the filter being in series;

cooling the breathing gas to a temperature below a temperature of a boiling point of the volatile anaesthetic agent when the breathing gas passes through the filter so as to condense the volatile anaesthetic agent out of the breathing gas;

warming the breathing gas after the volatile anesthetic agent is condensed; and leading the warmed breathing gas back into the main portion of the line system.

2. The method of claim 1, the step of warming comprising:

warming the breathing gas immediately after passing through the filter.

3. The method of claim 1, further comprising:

circulating the breathing gas in the line system at a speed such that a duration of one circulation of the breathing gas in the line system is no more than 10 seconds.

4. The method of claim 3, the duration of one circulation of the breathing gas in the line system is no more than 2.5 seconds.

5. An apparatus for respiration a patient with a breathing gas in which the breathing gas has an anesthetic agent therein, the apparatus comprising:

a line system in which a pressure of the breathing gas therein is varied in accordance with a respirating pattern of the patient, said line system having a first connector for supplying the breathing gas to the patient and a second connector adapted to connect with a supply of the breathing gas, the line system having a main portion that leads all of the breathing gas therethrough, a first portion communicating with the main portion, and a second portion communicating with the main portion, the second portion positioned parallel to the first portion;

a blower cooperative with said line system so as to circulate the breathing gas in the main portion, the first portion and the second portion;

an absorber positioned in the main portion of said apparatus so as to remove carbon dioxide from the breathing gas, the second portion of the line system having a filter device therein, said filter device having activated carbon so as to remove the anesthetic agent from the breathing gas, the absorber and the filter device being in series;

a cooler cooperative with said filter, said cooler adapted to cool the breathing gas so that the anesthetic agent condenses on said activated carbon of said filter device; and a warmer provided to warm the breathing gas after the anesthetic agent has condensed out of the breathing gas.

6. The apparatus of claim 5, said warmer positioned immediately after said filter device so as to warm the breathing gas immediately after the breathing gas passes through said filter device.

7. The apparatus of claim 5, said warmer being a Peltier element.

8. The apparatus of claim 5, wherein said blower cooperative with the breathing gas in said line system such that a duration of one circulation of the breathing gas in said line system is no more than 10 seconds.

9. The apparatus of claim 8, the duration of one circulation being no more than 2.5 seconds.

10. The apparatus of claim 8, said blower having a capacity of between 15 and 120 liters per minute.

11. The apparatus of claim 10, said blower having the capacity of between 30 and 60 liters per minute.

* * * * *